United States Patent [19]
Ozawa et al.

[11] Patent Number: 5,413,685
[45] Date of Patent: May 9, 1995

[54] ION-SELECTIVE ELECTRODE

[75] Inventors: Satoshi Ozawa, Mitaka; Yuji Miyahara, Hitachi; Mamoru Taki, Ibaraki; Koutarou Yamashita, Katsuta; Yoshio Watanabe, Kokubunji, all of Japan

[73] Assignee: Hitachi, Ltd., Tokyo, Japan

[21] Appl. No.: 128,236

[22] Filed: Sep. 29, 1993

[30] Foreign Application Priority Data

Oct. 2, 1992 [JP] Japan .................................. 4-264583

[51] Int. Cl.⁶ ............................................. G01N 27/333
[52] U.S. Cl. ...................................... 204/416; 204/418; 204/435
[58] Field of Search ............................... 204/416–420, 204/435

[56] References Cited

U.S. PATENT DOCUMENTS

| | | | |
|---|---|---|---|
| 2,934,484 | 4/1960 | Anderson | 204/435 |
| 3,574,078 | 4/1971 | Hynes et al. | 204/415 |
| 3,625,851 | 12/1971 | Geld | 204/435 |
| 3,700,577 | 10/1972 | Grauer | 204/435 |
| 3,856,649 | 12/1974 | Genshaw et al. | 204/418 |
| 4,214,968 | 7/1980 | Battaglia et al. | 204/435 |
| 4,227,984 | 10/1980 | Dempsey et al. | 204/421 |
| 4,776,944 | 10/1988 | Janata et al. | 204/418 |
| 5,011,588 | 4/1991 | Rao et al. | 204/418 |
| 5,074,988 | 12/1991 | Nyberg et al. | 204/418 |
| 5,288,388 | 2/1994 | Fombon | 204/418 |

Primary Examiner—T. Tung
Attorney, Agent, or Firm—Antonelli, Terry, Stout & Kraus

[57] ABSTRACT

An ion-selective electrode comprises an ion-sensing membrane, an internal electrode adhered to the ion-sensing membrane, and a lead connected to said internal electrode. The internal electrode used comprises a plurality of metallic wires arranged into a grating or a mesh. The wires comprises a metal core and a surface layer of a salt of the metal. The metal of the core is silver and the salt of the metal is a silver halide selected from the group consisting of silver bromide, silver chloride and silver iodide. At least a part of the internal electrode is buried inside the ion-sensing membrane. Various components, the ion-sensing membrane, the internal electrode, the lead, an external terminal, are disposed in a flow-through cell having a flow path formed therein, through which path a sample solution is passed, to constitute the ion-selective electrode. In the flow-through cell is disposed a means of maintaining the humidity to feed water vapor therefrom to the ion-sensing membrane. This structure, even when the ion-sensing membrane has a complicated configuration such as concave or convex surface, enables the establishment of good adhering conditions between the internal electrode and the ion-sensing membrane while retaining the complicated configuration of the ion-sensing membrane without reducing the effective contact areas of the ion-sensing membrane and the internal electrode.

23 Claims, 5 Drawing Sheets

ION-SELECTIVE ELECTRODE

BACKGROUND OF THE INVENTION

1. Field of the Invention

The present invention relates to an ion-selective electrode for use in electrochemical measurement of the amount of ions present in a sample solution, and more particularly, to a structure of an internal electrode in the ion-selective electrode having an ion-sensing membrane in a complicated configuration.

2. Description of the Related Art

There have been two types of ion-selective electrode having an ion-sensing membrane: the first type ion-selective electrode has an internal electrolyte solution or internal electrolyte gel on the side opposite to the ion-sensing membrane, which will contact with a sample solution, and is capable of making an electrochemical contact with an internal electrode consisting of silver/silver chloride and the like via the internal electrolyte solution or the internal electrolyte gel; and the second type ion-selective electrode has no internal electrolyte solution, nor internal electrolyte gel on the side opposite to the ion-sensing membrane which will contact with a sample solution, but is capable of making an electrochemical contact directly with the internal electrode consisting of silver/silver chloride and the like. Comparing with the first type ion-selective electrode, the second type one is characterized in that it has a simpler structure and can be easily compacted because of having no internal electrolyte solution. Many ion-selective electrodes of the second type have been known, as disclosed in, for example, JP 58-86449A where a flow-through cell type ion-selective electrode was produced by forming an ion-sensing membrane on the internal surfaces of a cylindrical internal electrode; JP 63-37251A where an ion-selective electrode of the flow-through cell type having a similar structure is disclosed; JP 61-180133A where an attempt is made to enhance the stability and the measurement accuracy of the flow-through cell type ion-selective electrode by providing an ion-sensing membrane projecting convexly into the flow path.

When the ion-sensing membrane is disposed projecting convexly into the flow path of a sample solution, the projection formed to have a smoothly curved surface can facilitate exchanges of samples at the ion-sensing membrane while preventing the flow of the sample solutions from stagnating, which is effective to speed up the response of the ion-selective electrode. However, there is still a problem that it is not easy to make the ion-sensing membrane in a complex three-dimensional form, for example, in a projecing form having a smoothly curved surface. In one of simplest techniques to solve the problem, the flow-through cell may be made of a resin such as poly(vinyl chloride) and shaven along a curved surface projecing into the flow path. An ion-sensing membrane may be separately produced and adhered on the opposite side of the shaven curved surface to the flow path making use of the membrane's flexibility. Then a plate-like internal electrode is adhered on the back side of the ion-sensing membrane to produce an ion-selective electrode. However, the internal electrode made of a metal plate having a sufficient mechanical strength is less flexible so that a gap is apt to be formed between the ion-sensing membrane and the internal electrode unless the configuration of the internal electrode is precisely consistent with the shaven curved surface. Once the gap is formed, a failure in adhesion may be caused during the production of the ion-selective electrode, or the repetition of the use of the ion-selective electrode may render the ion-sensing membrane liable to be peeled off. Therefore, there remains a problem to be solved. An attempt has been made to overcome this problem by making the surface area of a disk-like internal electrode smaller and coating the circular periphery of the disk-like internal electrode with the same polymeric material as the matrix of the ion-sensing membrane so that any gap which might be formed during adhering the internal electrode to the ion-sensing membrane is made smaller to achieve a better adhesion between the internal electrode and the ion-sensing membrane and to ensure good adhering conditions, thereby preventing the adhered regions from delaminating. This technique produces problems that the good gapless adhesion between the internal electrode and the ion-sensing membrane can be achieved at the cost of the effective contacting surface area of the internal electrode and that when an ion-sensing membrane having a high impedance is used, the resultant ion-selective electrode is susceptible to noise generation.

SUMMARY OF THE INVENTION

An object of the present invention is to provide an ion-selective electrode where good adhering conditions between an internal electrode and an ion-sensing membrane can be achieved even when the ion-sensing membrane has a complicated configuration such as concave or convex surface without reducing the effective contact areas of the ion-sensing membrane and the internal electrode in contact therewith in the ion-selective electrode.

DETAILED DESCRIPTION OF PREFERRED EMBODIMENTS

The objects as described above can be achieved by providing a structure comprising an internal electrode which may be manufactured by using fine metal wires as a basic material for the electrode and arranging the wires two or three dimensionally, at least a part of the electrode being buried in an ion-sensing membrane. That is, there is provided an ion-selective electrode comprising an ion-sensing membrane, an internal electrode in contact with the ion-sensing membrane, and a lead connected to the internal electrode, where the internal electrode comprises a frame produced by arranging a plurality of metal wires two or three dimensionally, practically into the form of grating or mesh. The frame may consist of a combination of a plurality of elements in the form of grating or mesh produced by arranging the wires two or three dimensionally. The wires constituting the internal electrode may comprise a metal core and a surface layer consisting of a salt of the same metal as that of the core. The metal of the core is silver and the metal salt of the surface layer is a silver halide selected from the group consisting of silver bromide, silver chloride, and silver iodide. At least a part of the internal electrode is buried in the ion-sensing membrane. Moreover, there is provided a flow-through cell having a flow path, though which a sample solution is passed to contact the ion-sensing membrane. To the flow-through cell, various components such as the ion-sensing membrane, the internal electrode, the leads and the external terminals are attached to complete a flow-through cell type ion-selective electrode. Inside the flow-through cell may be disposed a means for maintaining the humidity which serves to feed water vapor to the ion-sensing membrane.

In another embodiment of the arrangement of the ion-selective electrode, the internal electrode and the ion-sensing membrane are not allowed to contact with each other, but separated from each other with a hydrophilic material interposed therebetween, or alternatively, at least a part of the internal electrode is in contact with the ion-sensing membrane, or buried in the ion-sensing membrane. Hydrated hydrophilic members may be disposed in at least a part of the interspaces (or the openings of the mesh) of the internal electrode so that the hydrated hydrophilic members can be in contact with at least a part of the ion-sensing membrane. The hydrated hydrophilic members may comprise a hydrated hydrophilic polymer, or a dispersion of a water soluble salt in a hydrated hydrophilic polymer.

The internal electrode consisting of fine metal wires arranged two or three dimensionally has a higher tensile strength and a higher breaking strength, and generally a very lower repulsive force (elastic force) against bending as compared with those consisting of the same metal sheet having the same thickness. This is because the internal electrode consisting of fine metal wires allows the individual fine wires to relatively easily displace and rotate so as to take stable positions and angles when any stress is applied externally. For example, even if the ion-sensing membrane has a complicated configuration such as concave or convex surface, the internal electrode can be easily deformed and adapted to desired shape. As a result, the ion-sensing membrane and the plate-like internal electrode can be used scarcely causing the problem of generating any gap owing to the mismatch in configuration therebetween, which gap may cause separation of the adhered regions, so that good adhering conditions between the ion-sensing membrane and the internal electrode can be retained.

Of course, when the elements produced by arranging the fine metal wires two or three dimensionally are used for the internal electrode, a part or all of the internal electrode may be buried in the ion-sensing membrane making it possible to retain a very large effective contact area between the internal electrode and the ion-sensing membrane.

In summary, the present invention provides a flow-through cell having a flow path formed, through which a sample solution to be analyzed is passed, and having an ion-sensing membrane, internal electrode, leads and terminals disposed in the cell. The internal electrode may be of a mesh type and at least a part of the internal electrode is buried in the ion-sensing membrane. The internal electrode comprises an element produced by arranging fine metal wires into a mesh. Such a structure allows ensuring good contact conditions between the ion-sensing membrane and the internal electrode while retaining the complicated configuration of the ion-sensing membrane without reducing the effective contact area between the internal electrode and the ion-sensing membrane.

The present invention will be illustrated below with reference to Examples and FIGS. 1 to 10.

Example 1

Figure 1:
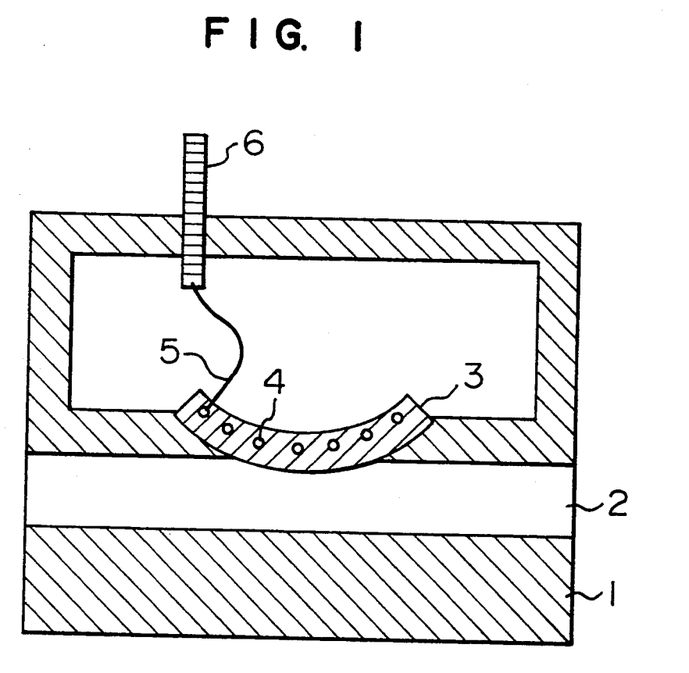
FIG. 1 is a cross-sectional view of the ion-selective electrode as described in Example 1 according to the present invention.

FIG. 1 is a cross-sectional view of one of embodiments of the ion-selective electrode according to the present invention. Flow-through cell 1 has a flow path 2 formed, through which a sample solution is passed, and has an ion-sensing membrane 3, an internal electrode 4, a lead 5 and an external terminal 6 disposed. The internal electrode 4 in the form of a mesh is buried in the ion-sensing membrane 3. In FIG. 1 there are shown cross-sections of the fine wires constituting the mesh.

Figure 2:
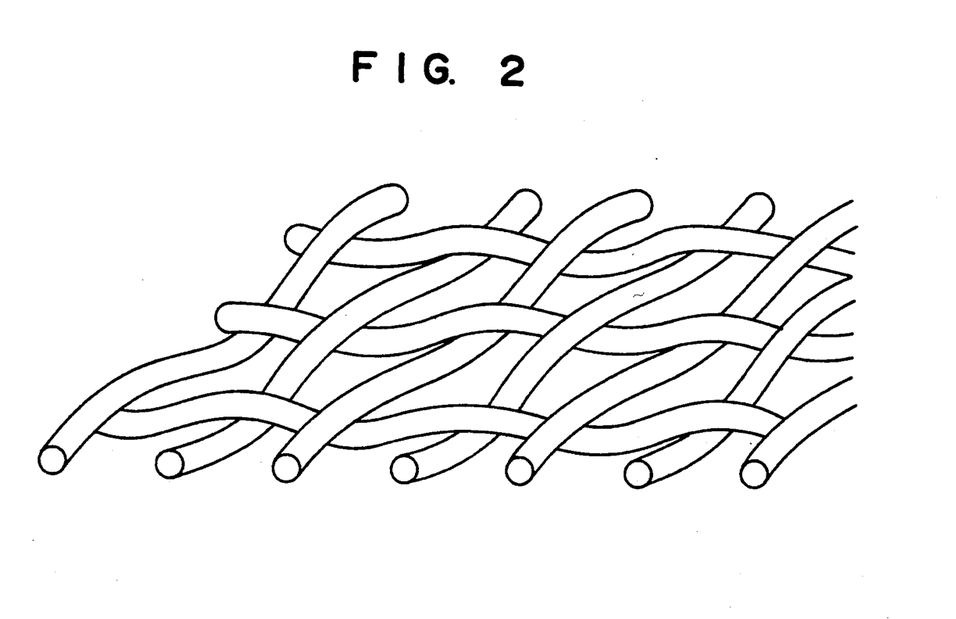
FIG. 2 is a perspective view of a material for the internal electrode as described in Example 1 according to the present invention.

Next a process for producing the ion-selective electrode in this example will be described. The internal electrode 4 comprises a member produced by knitting silver wires of 0.05 mm in diameter into a mesh as shown in FIG. 2. The lead 5 is a silver wire of 0.05 mm in diameter. First, the internal electrode 4 is connected to the lead 5 by spot welding and then the silver wires being in contact with the ion-sensing membrane 3 are subjected to an electrolysis to produce silver bromide on the surfaces of the silver wires. By the electrolysis, the surface of a part of the lead 5 is converted into silver bromide, which partly functions as an internal electrode to be included in the internal electrode 4 rather than in the lead 5 in this example.

The internal electrode 4 produced as described above is buried inside the ion-sensing membrane 3 in the following procedure (the first embodiment of the process for manufacturing a unitary assembly of the internal electrode and the ion-sensing membrane): Valinomycin as a potassium ion-sensing compound, potassium tetrakis(p-chlorophenyl) borate as an additive, dioctyl adipate as a plasticizer, and poly(vinyl chloride) having a mean degree of polymerization of about 1000 as matrix are weighed in a ratio by weight of 1:0.3:66:33, mixed with an addition of 4 ml of tetrahydrofuran and dissolved to produce a stock solution for the production of membrane. On a glass plate is placed a glass ring having a diameter of 30 mm, into which a half of the stock solution is poured and left to stand to evaporate tetrahydrofuran, whereby an ion-sensing membrane (lower membrane) is obtained.

The internal electrode 4 produced by the aforementioned process is placed on the ion-sensing membrane (lower membrane) within the glass ring with the flat mesh side being lower side and the lead-attached side being upper side. Then the mesh side of the internal electrode is tightly contacted with the ion-sensing membrane (lower membrane) to form an assembly. Then the remaining half of the stock solution is gradually poured onto the assembly. The solution flows not only on the internal electrode, but also into the interstices between the ion-sensing membrane (lower membrane) and the internal electrode as well as the openings of the internal mesh electrode. The upper surface of the ion-sensing membrane (lower membrane) is partly redissolved, but the tetrahydrofuran evaporates to produce the ion-sensing membrane 3.

In the thus produced ion-sensing membrane, the lower membrane and the upper portion have the same composition, so that there is actually no distinction therebetween. Therefore, the ion-sensing membrane is made unitary. This ion-sensing membrane is formed in the manner that it comprises three layers, i.e., about 150 $\mu m$ in thickness between the glass surface and the bottom surface of the mesh of the internal electrode, about 100 $\mu m$ in thickness within the mesh layer and about 100 $\mu m$ in thickness above the upper surface of the internal electrode with the internal electrode being included in the three layers.

Next, the assembly consisting of the ion-sensing membrane 3, the internal electrode 4, and the lead 5 is removed from the glass ring and cut into a disk having a diameter of about 5 mm including the lead. This disk member is adhered with tetrahydrofuran to the flow-through cell 1 in the manner that the surface of the disk which has been in contact with the glass plate is facing to the flow path 2 as shown in FIG. 1. Finally, the free end of the lead is soldered to the external terminal 6 and then all other parts of the flow-through cell than the inlet and outlet of the flow path 2 are sealed to complete the flow-through cell for potassium ion. Since the weld portion between the lead 5 and the internal electrode 4 may have an irregular shape, it is disposed somewhere except the region where the ion-sensing membrane 3 is in contact with the path 2. In this way, a part of the ion-sensing membrane 3 is exposed to the flow path 2 to be able to contact with a sample solution flowing therein.

Operation of this ion-selective electrode will be explained. A sample solution is introduced into the flow path 2 of the flow-through cell 1 and it will contact the ion-sensing membrane 3. As a result, a membrane potential ($E_1$) generates between the ion-sensing membrane and the sample solution corresponding to the activity of potassium ion in the sample solution. The output potential (E) at the external terminal 6 is the sum of the membrane potential ($E_1$) and the potential generating between the ion-sensing membrane and the internal electrode ($E_2$). Since the latter ($E_2$) may be regarded constant, however, the influence thereof may be neglected.

A reference electrode can be provided adjacent the flow-through cell 1 permitting measurement of the differential potential between the external terminal 6 and the reference electrode to observe a potential depending upon the activity of the potassium ions in the sample solution. Using a calibration curve obtained by measuring standard solutions, the activity of potassium ions in a sample solution having an unknown concentration can be determined.

In this embodiment non-plasticized poly(vinyl chloride) was used as material for the flow-through cell 1 and the flow path 2 was molded unitary with the flow-through cell by molding. However, the material for the flow-through cell is not limited to poly(vinyl chloride), but any materials can be similarly used so long as they have an appropriate hardness. The formation of the flow path may be performed by any one of techniques other than the unitary molding, such as drilling, connecting of a plurality of materials, and the like.

For ion-sensing membrane 3 of this embodiment a self-supporting polymer liquid membrane type of ion-sensing membrane with valinomycin as a ion-sensitive compound was used. Of course, other ion-sensing membrane may be employed. The ion-sensitive compounds to be used include cyclic or acyclic antibiotics such as nonactin, monactin, and monensin; synthetic ionophores such as various crown ethers, dibutylphenantrolin, phenylphosphoric esters, and acyclic diamines; and ion-exchange type ligands such as quaternary ammonium salts and various phosphate salts. The plasticizers to be used include various dicarboxylic acid esters, nitrobenzene, acetophenone, derivatives thereof, and alkyl alcohols having not less than 10 carbon atoms besides dioctyl adipate. The additives to be used include tetraphenylborate salt, tetrakis[bis(trifluoromethyl)-phenyl]borate salt, and the like besides tetrakis(p-chlorophenyl)borate salt. The matrixes to be used include polycarbonates, silicone resins, epoxy resins and the like besides poly(vinyl chloride).

Figure 3:
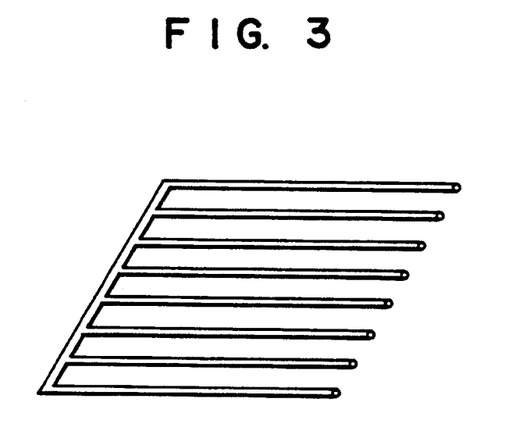
FIG. 3 is a perspective view of a comb type internal electrode with one edge thereof being fixed.
Figure 4:
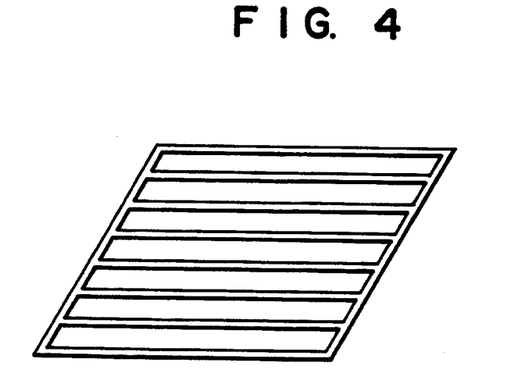
FIG. 4 is a perspective view of a grating type internal electrode with both edges thereof being fixed.

The internal electrode 4 used in this Example comprises the member produced by knitting silver wires of 0.05 mm in diameter into a mesh and then converting the surfaces thereof into silver bromide. However, the process for producing the internal electrode is not limited to such as described above. Metal materials to be used include gold, platinum, iridium, rhodium, ruthenium, copper, nickel, alloys thereof, as well as alloys thereof with mercury, besides silver. The metal member may have any one of configurations other than the mesh type produced by knitting wires such as a comb-like shape with parallel rods being fixed at one edge thereof as shown in FIG. 3, or a grating shape with parallel rods being fixed at both edges thereof as shown in FIG. 4, or a composite obtained by arranging two or three dimensionally the aforementioned shapes. When the wires are sufficiently small in diameter, they may be employed as they are, but when they are thick, the mesh may be rolled to have thinner openings and then used preferably after annealed to restore the flexibility. The surface layer of the internal electrode should be composed of any one of the salts consisting of the ions of the metal material of the internal electrode and anions, preferably such as silver halides, for example, silver chloride, silver bromide, silver sulfide, and mercury halides. Most preferably silver bromide should be used. The formation of the surface layer can be accomplished conveniently and reliably by electrolysis. Alternatively, it may be achieved by producing a salt by precipitation and then adhering under pressure onto the surfaces of the internal electrode.

For the lead in this Example there was used a silver wire having a diameter of 0.05 mm, but a metal of other shape may be employed without any obstruction. The metal to be used should preferably be of the same sort as that used for the internal electrode. The connection between the lead and the internal electrode should preferably be achieved by spot welding, though any other methods such as wrapping or soldering may be employed insofar as an electrical communication can be established between the lead and the internal electrode. Alternatively, a part of the wire itself constituting the mesh may be used as a lead.

In this Example, the internal electrode 4 was buried in the ion-sensing membrane 3 to form a unitary assembly. The way of forming the unitary assembly is not limited to the aforementioned process. The second process to be preferably employed for producing the assembly will be explained. In a glass ring placed on a glass plate, there is suspended a internal electrode parallelly to the glass plate with a gap of about 100 μm being present between the internal electrode and the surface of the glass plate. The stock solution for ion-sensing membrane is poured onto the suspended internal electrode to flow into all the interspaces, the openings of the mesh as well as over the internal electrode. After the tetrahydrofuran solvent is evaporated, the ion-sensing membrane and the internal electrode are formed as a unitary assembly with the latter being buried in the former. Alternatively, the third process for producing the assembly will be explained. The stock solution for ion-sensing membrane is divided into two a half aliquots, each of which is cast into an ion-sensing membrane having a half thickness. Two ion-sensing membranes produced in this way are adhered to both sides of the internal electrode. As solvent in the adhering, tetrahydrofuran or a solution of the material of the ion-sensing membrane in tetrahydrofuran should preferably be used. The fourth process for producing the assembly is as follows. The previously prepared stock solution for ion-sensing membrane is poured in one portion into the glass ring, and then an internal electrode is forced into the pool of the solution. At that time, the internal electrode can be submerged into the solution so long as the solvent, tetrahydrofuran is not evaporated from the solution. Even after the tetrahydrofuran was evaporated, the internal electrode can be buried in the ion-sensing membrane while dissolving the surfaces thereof by adding further the solvent onto the membrane or forcing the internal electrode into the ion-sensing membrane after adhering the solvent to the internal electrode.

In this Example, the ion-sensing membrane buried in the internal electrode produced in this way is adhered to the flow path of the flow-through cell around the periphery of the opening provided in the flow path to obtain the ion-selective electrode. The way to connect the ion-sensing membrane, the internal electrode and the periphery of the opening of the flow path is not limited to the aforementioned process. In another process for the connection, for example, the ion-sensing membrane may first be adhered to the flow-through cell and then the internal electrode may be adhered to the ion-sensing membrane by the third or fourth process as described above.

The embodiment as described in this Example has the following unique effects. The burying of the internal electrode inside the ion-sensing membrane as in this Example allows almost all the surfaces of the fine wires constituting the internal electrode, except a very small portion where the fine wires contact with one another, can be in contact with the ion-sensing membrane. In this way it is possible to retain a large contacting area between the internal electrode and the ion-sensing membrane, so that the boundary impedance can be minimized and even with an ion-sensing membrane of a high impedance one can achieve a high accuracy measurement with less noise.

Moreover, this embodiment allows the establishment of good adhering conditions between the ion-sensing membrane and the internal electrode. The present invention does not necessarily require that the internal electrode is buried inside the ion-sensing membrane, but only a part of the wire material constituting the internal electrode may be in contact with the ion-sensing membrane. Comparing with such case, this embodiment where almost all the surfaces of the internal electrode are in contact with the ion-sensing membrane can naturally achieve extremely superior contacting conditions between the internal electrode and the ion-sensing membrane. Therefore, the connection portion of the internal electrode and the ion-sensing membrane has less tendency to break apart even after repeatedly using the ion-selective electrode.

Example 2

Figure 5:
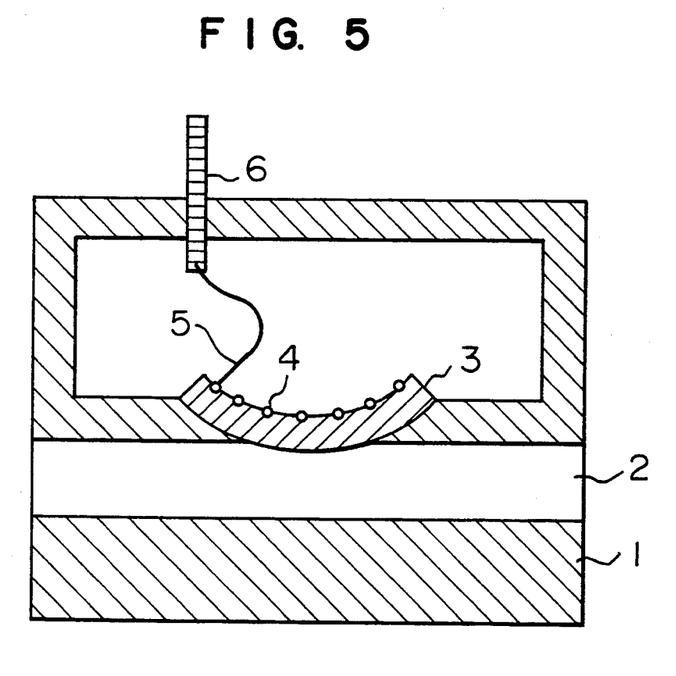
FIG. 5 is a cross-sectional view of the ion-selective electrode as described in Example 2 according to the present invention.

Second embodiment of the present invention will be illustrated with reference to FIG. 5. FIG. 5 is a cross-sectional view of the ion-selective electrode in this Example according to the present invention. Individual component has the identical configuration and function to those in Example 1, except that in this Example 2, the internal electrode 4 is not perfectly buried in the ion-sensing membrane 3, but partly exposed to the space opposite to the flow path 2. Since all the portions or internal electrode are not buried in the ion-sensing membrane, one can not employ the third process for connecting the internal electrode to the ion-sensing membrane among those described in Example 1, i.e., two ion-sensing membranes being adhered to both sides of the internal electrode to sandwich the latter. The first process can be performed by controlling the amounts of the stock solution to be used in the first and second pouring steps so that all the surfaces of the internal electrode are not covered. The second process can be performed by controlling the level of the suspended internal electrode and the amount of the stock solution to be poured into. The fourth process can be performed by controlling the depth of the submerged internal electrode in the stock solution. The embodiment of this Example can achieve the following unique effects: As there is no need to render the thickness of the internal electrode not larger than that of the ion-sensing membrane, relatively easily available thicker metallic wires can be used to knit a mesh member which can be used as an internal electrode. Moreover, as there is no need to bury the overall internal electrode inside the ion-sensing membrane, the thickness of the ion-sensing membrane and the distance between the internal electrode and the flow path can be more freely selected allowing the ready production of the ion-selective electrode.

Example 3

Figure 6:
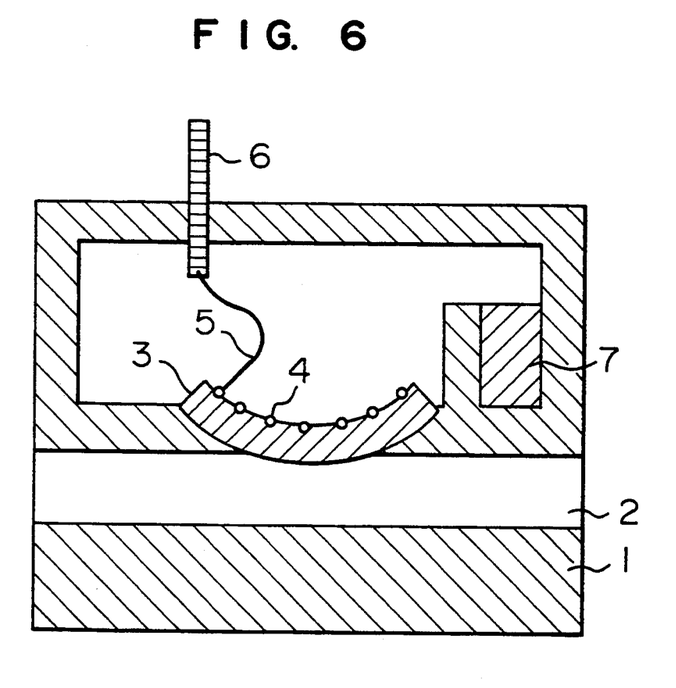
FIG. 6 is a cross-sectional view of the ion-selective electrode as described in Example 3 according to the present invention.

Third embodiment of the present invention will be illustrated with reference to FIG. 6. FIG. 6 is a cross-sectional view of the ion-selective electrode in this Example according to the present invention. This embodiment is identical to those in Examples 1 and 2, except that in this embodiment, a means of maintaining the humidity 7 is disposed inside the flow-through cell 1. In this case, the means of maintaining the humidity functions by releasing water vapor. Preferably, materials to be used for the means of maintaining the humidity are hydrophilic organic polymers which can be impregnated with water, such as agarose, poly(vinyl alcohol), poly(acrylamide), poly(styrene sulfonic acid), or inorganic silicate salts. This embodiment can achieve the following unique effects: The water vapor evaporated from the humidity-maintaining member can highly efficiently be fed to the ion-sensing membrane through the openings in the mesh-like internal electrode ensuring the stable operation of the ion-sensing membrane, so that the ion-selective electrode can stably operate even when the ion-sensing membrane needs moisture to achieve stable function, and can be preserved under consistent conditions.

Example 4

Figure 7:
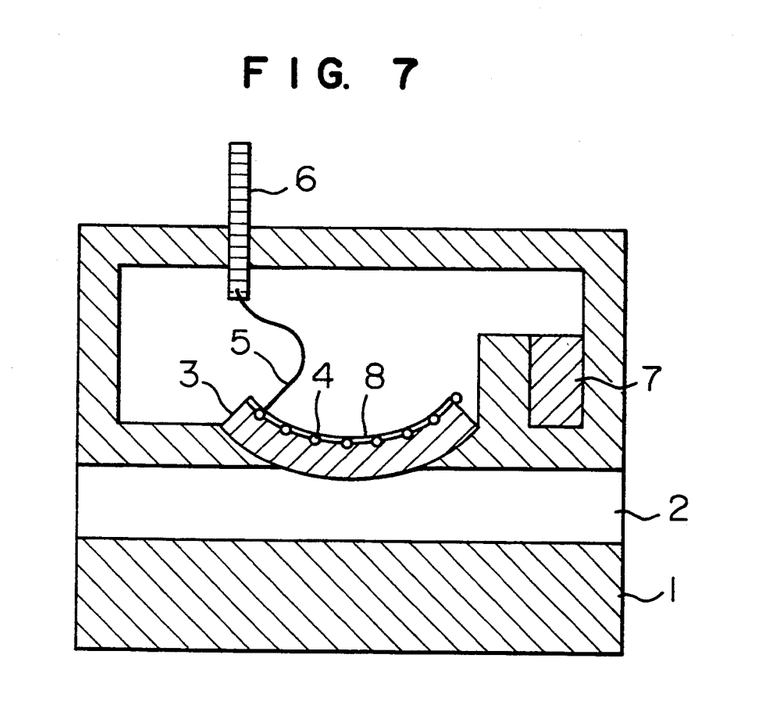
FIG. 7 is a cross-sectional view of the ion-selective electrode as described in Example 4 according to the present invention.

Fourth embodiment of the present invention will be illustrated with reference to FIG. 7. FIG. 7 is a cross-sectional view of the ion-selective electrode in this Example according to the present invention. This embodiment is identical to that in Example 3, except that in this embodiment, the hydrophilic member 8 is disposed within the interspaces of the internal electrode 4 to be in contact with the ion-sensing membrane 3. This hydrophilic member 8 is composed of a hydrophilic polymer with a small amount of the water of hydration, or of a hydrophilic polymer, a water soluble salt and a small amount of the water of hydration. The hydrophilic member may be produced by evaporating an excess water from an aqueous solution of a hydrophilic polymer, or from an aqueous solution of a hydrophilic polymer and a water soluble salt. Although poly(vinyl alcohol) was used in this Example, the hydrophilic polymers to be used include preferably further gelatin, agarose, poly(acrylamide), poly(vinylpyrolydone), poly(hydroxyethyl methacrylate), poly(hydroxyethyl acrylate), poly(acrylic acid). Of course, they may be used alone or in a combination of a plurality thereof. The water soluble salts to be used, though potassium bromide was used in this Example, include preferably sodium chloride, potassium chloride, sodium bromide, ammonium chloride, tetramethylammonium chloride, and sodium tetraphenylborate besides potassium bromide. Of course, these may be used alone or in a combination of a plurality thereof. The cations constituting the water soluble salts include alkali metal ions, alkaline earth metal ions, ammonium ion and various quaternary ammonium ions which may be used alone or in a combination thereof. The anions constituting the water soluble salts include various halide, nitrate, nitrite, thiocyanate, perchlorate, sulfate, hydrogen phosphate, and various tetraarylborate ions which may be used alone or in combination thereof. Moreover, as cations for the water soluble salts, there may be used alone or in a combination the cations from alkali metal ions, alkaline earth metal ions, ammonium ion and various quaternary ammonium ions, and as anions for the water soluble salts, there may be used alone or in combination the anions from various halide, nitrate, nitrite, thiocyanate, perchlorate, sulfate, hydrogen phosphate, and various tetraarylborate ions excluding those anions of the metal salts used in the surface layer of the wires constituting the internal electrode in this Example, or the intermediate materials for the wires constituting the internal electrode as described later in Example 5. In this Example, as a part of the internal electrode is in direct contact with the ion-sensing membrane, the water soluble salts are not indispensable, but can be omitted without affecting the normal operation of the ion-selective electrode. The unique effects achieved by this embodiment are as follows: Since the hydrophilic member 8 is in direct contact with the ion-sensing membrane, the water retention in the hydrophilic member is facilitated, so that even when the moisture is required to operate stably the ion-sensing membrane, the ion-sensing membrane can be preserved under stable conditions to work consistently. Moreover, when the water soluble salts are added to the hydrophilic member, the hydrophilic member becomes electroconductive so that the transmission of the electrode potential can easily be achieved.

Example 5

Figure 8:
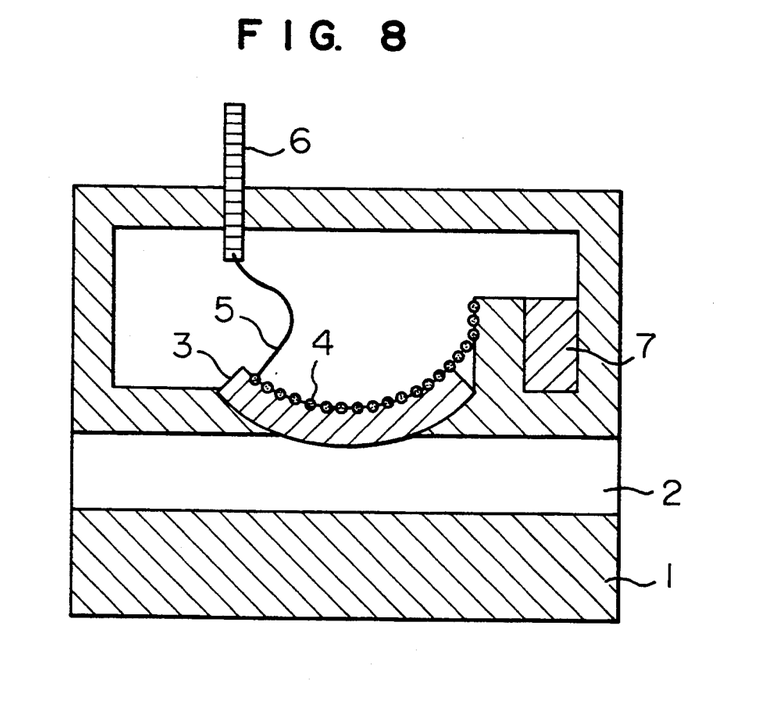
FIG. 8 is a cross-sectional view of the ion-selective electrode as described in Example 5 according to the present invention.
Figure 9:
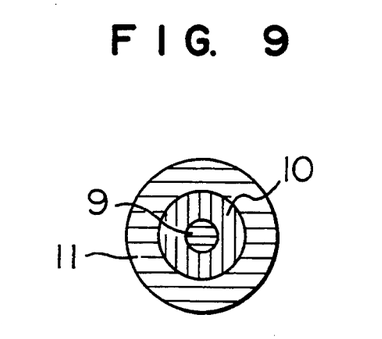
FIG. 9 is a cross-sectional view of the wire component for the internal electrodes as described in Examples 5 and 6 according to the present invention.

Fifth embodiment of the present invention will be illustrated with reference to FIGS. 8 and 9. FIG. 8 is a cross-sectional view of the ion-selective electrode in this Example according to the present invention and FIG. 9 is a cross-sectional view of the wire member constituting the internal electrode in this Example. This embodiment is identical to those in Examples 1 to 4, except that in this embodiment, the wire member used to constitute the mesh-like internal electrode 4 comprises a core element 9 of silver, an intermediate material 10 of silver bromide and a surface layer 11 of a hydrophilic material as shown in FIG. 9. Such a hydrated hydrophilic member can be used in place of the internal electrolyte solution within the prior ion-selective electrode as reported by Smith et al. in Analytical Chemistry, 45, No. 9, pp. 1782–1784 (1973). The hydrated polymer material (hydrophilic member) as disclosed in this literature can be used in the surface layer of the internal electrode of the ion-selective electrode in this Example, as shown in FIG. 8, without affecting the normal operation thereof. However, the above literature discloses the use of linear internal electrode and does not take into consideration the structure (mesh or the like) of the internal electrode which is characteristic of the present invention. In this embodiment, the hydrophilic material used for forming the surface layer 11 was a dispersion of potassium chloride in poly(vinyl alcohol), though a combination of other hydrophilic polymers and other water soluble salts may be used as in Example 4. In Example 5, however, the water soluble salts can not be omitted because the surface layer 11 must have electroconductivity. In this embodiment, the anion (bromide ion) in the intermediate material of the wire member constituting the internal electrode is different from that (chloride ion) of the water soluble salts in the hydrophilic member. The use of different ions in this way permits the absolute value of the output potential of the ion-selective electrode to change, and therefore, it enables the output potential of the ion-selective electrode to be adjusted to be in the range suitable for the input to the apparatus which determines the potential and conducts various measurements. When the hydrophilic material is used in the surface layer of the internal electrode as in this Example, the contact between the internal electrode and the ion-sensing membrane may be instable. It is possible, however, to ensure the tight adhesion between the internal electrode and the ion-sensing membrane by fixing with adhesive an end of the internal electrode onto a portion of the flow-through cell as shown in FIG. 8. This embodiment has the following unique advantages: Since the hydrophilic surface layer 11 is in direct contact with the ion-sensing membrane, the retention of moisture in the surface layer 11 is facilitated, so that even when the moisture is required to operate stably the ion-sensing membrane, the ion-sensing membrane can be preserved under stable conditions to function consistently.

Example 6

Figure 10:
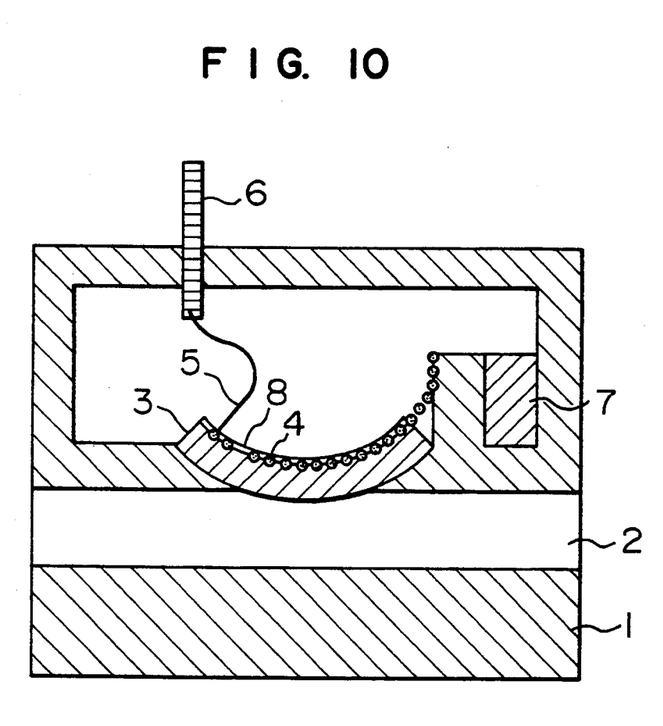
FIG. 10 is a cross-sectional view of the ion-selective electrode as described in Example 6 according to the present invention.

Sixth embodiment of the present invention will be illustrated with reference to FIG. 10. FIG. 10 is a cross-sectional view of the ion-selective electrode in this Example according to the present invention. This embodiment is corresponding to a combination of the embodiments as shown in Examples 4 and 5 and identical to that in Example 3, except that in this embodiment, the wire member used to constitute the mesh-like internal electrode 4 comprises a core element 9 of silver, an intermediate material 10 of silver bromide and a surface layer 11 of a hydrophilic material as shown in FIG. 9 and that the hydrophilic material 8 is disposed in the interspaces of the internal electrode 4 to be in contact with the ion-sensing membrane 3. In this Example, the hydrophilic material 8 and the surface layer 11 are composed of a dispersion of potassium chloride in poly(vinyl alcohol) as in Example 5, so that there is practically no distinction between the materials for the hydrophilic material and the surface layer. Of course, as in Examples 4 and 5, a combination of other hydrophilic polymers and other water soluble salts may be used, and different materials may be used in the hydrophilic material and the surface layer, respectively. Again in this Example, the water soluble salts can not be omitted in the surface layer 11 because the surface layer 11 must have electroconductivity. In this Example, as shown in FIG. 10, it is possible to ensur the tight adhesion between the internal electrode and the ion-sensing membrane by fixing with adhesive an end of the internal electrode onto a portion of the flow-through cell. This embodiment has the following unique advantages: Since the hydrophilic member 8 and the hydrophilic surface layer 11 are in direct contact with the ion-sensing membrane, the retention of moisture in the surface layer 11 is facilitated, so that even when the moisture is required to operate stably the ion-sensing membrane, the ion-sensing membrane can be preserved under stable conditions to function consistently. According to the present invention, by employing the means to maintain the ion-sensing membrane in a humid state, ion-selective electrode can stably operate in every case the ion-sensing membrane requires moisture to achieve stable function.

What is claimed is:

1. A flow-through cell for electrochemical measurement of ion concentration in a sample solution, comprising:
   a flow path through which the sample solution flows;
   an internal space separated from said flow path;
   an ion-sensing membrane having a curved portion projecting through an opening from said internal space into said flow path;
   an internal electrode comprising a plurality of metallic wires arranged at least two dimensionally with interspaces therebetween, said internal electrode being deformable, being at least partly buried in said ion-sensing membrane and detecting an electrical potential of said ion-sensing membrane;
   an external terminal; and
   a lead connecting said internal electrode to said external terminal.

2. A flow through cell according to claim 1, wherein said internal electrode is completely buried in said ion-sensing membrane.

3. A flow through cell according to claim 1, wherein said internal electrode is only partly buried in a surface of said ion-sensing membrane opposite to another surface projecting into said flow path, such that an upper surface of said internal electrode is exposed in said internal space.

4. A flow through cell according to claim 3, further comprising a hydrophilic member in said interspaces between said plurality of metallic wires and in contact with said ion-sensing membrane.

5. A flow through cell according to claim 4, wherein said hydrophilic member is made of at least one hydrophilic material selected from the group consisting of gelatin, agarose, poly (vinyl alcohol), poly (acrylamide), poly (vinylpyrolydone), poly (hydroxyethyl methacrylate), poly (hydroxyethyl acrylate) and poly (acrylic acid).

6. A flow through cell according to claim 5, wherein said hydrophilic member is made of said at least one hydrophilic material and a water soluble salt.

7. A flow through cell according to claim 6, wherein said water soluble salt is composed of at least one cation selected from the group consisting of alkali metal ions, alkaline earth metal ions, ammonium ion and quaternary ammonium ions and at least one anion selected from the group consisting of halide, nitrate, nitrite, thiocyanate, perchlorate, sulfate, hydrogen phosphate and tetraarylborate ions.

8. A flow through cell according to claim 4, further comprising a humidity maintaining member made of a hydrophilic organic polymer impregnated with water provided in said internal space and out of contact with said ion-sensing membrane for releasing water vapor and maintaining humidity in said internal space.

9. A flow through cell according to claim 8, wherein said hydrophilic organic polymer is selected from the group consisting of agarose, poly (vinyl alcohol), poly (acrylamide) and poly (styrene sulfonic acid).

10. A flow through cell according to claim 1, wherein said plurality of wires of said internal electrode are knitted in a form of a mesh.

11. A flow through cell according to claim 1, wherein said plurality of wires of said internal electrode are arranged in a comb-like shape in which each of the plurality of wires is fixed at one end to a metal member.

12. A flow through cell according to claim 1, wherein said plurality of wires of said internal electrode are arranged in a grating shape in which each of the plurality of wire is fixed at both ends to metal members.

13. A flow through cell according to claim 1, wherein said plurality of metal wires have a core made of at least one metal selected from the group consisting of silver, gold, platinum, iridium, rhodium, ruthenium, copper and nickel.

14. A flow through cell according to claim 13, wherein said plurality of metal wires have a core of an alloy of said at least one metal and mercury.

15. A flow through cell according to claim 14, wherein said internal electrode has a surface layer made of a salt of said at least one metal or a salt of mercury.

16. A flow through cell according to claim 13, wherein said internal electrode has a surface layer made of a salt of said at least one metal.

17. A flow through cell according to claim 13, wherein said plurality of metal wires have a silver core and said internal electrode has a surface layer made of a material selected from the group consisting of silver halide, mercury halide and silver sulfide.

18. A flow through cell according to claim 17, wherein said surface layer is made of a material selected from the group consisting of silver chloride, silver bromide and silver iodide.

19. A flow through cell according to claim 1, further comprising a humidity maintaining member made of a hydrophilic organic polymer impregnated with water provided in said internal space and out of contact with said ion-sensing membrane for releasing water vapor and maintaining humidity in said internal space.

20. A flow through cell according to claim 19, wherein said hydrophilic organic polymer is selected from the group consisting of agarose, poly (vinyl alcohol), poly (acrylamide) and poly (styrene sulfonic acid).

21. A flow through cell according to claim 1, wherein said plurality of wires have a core made of at least one metal selected from the group consisting of silver, gold, platinum, iridium, rhodium, ruthenium, copper and nickel, and said internal electrode has an intermediate layer of made of a salt of said at least one metal, and a surface layer made of hydrated hydrophilic material.

22. A flow through cell according to claim 21, further comprising a humidity maintaining member made of a hydrophilic organic polymer impregnated with water provided in said internal space and out of contact with said ion-sensing membrane for releasing water vapor and maintaining humidity in said internal space.

23. A flow through cell according to claim 22, further comprising a hydrophilic member in said interspaces between said plurality of metallic wires and in contact with said ion-sensing membrane.

* * * * *